United States Patent
Spitzer-Keller et al.

(10) Patent No.: US 7,435,702 B2
(45) Date of Patent: Oct. 14, 2008

(54) PHOTOCATALYST AND PROCESS FOR PURIFYING GAS EFFLUENT BY PHOTOCATALYTIC OXIDATION

(75) Inventors: Valerie Spitzer-Keller, Strasbourg (FR); Pierre Bernhardt, Heiligenberg (FR); Cuong Pham-Huu, Savernes (FR); Francois Garin, Schiltigheim (FR); Marc J. Ledoux, Strasbourg (FR); Charlotte Pham-Huu, Savernes (FR)

(73) Assignees: SICAT, Paris (FR); Centre National de la Recherche Scientifique, Paris (FR); Universite Louis Pasteur de Strasbourg, Strasbourg (FR)

( * ) Notice: Subject to any disclaimer, the term of this patent is extended or adjusted under 35 U.S.C. 154(b) by 221 days.

(21) Appl. No.: 10/380,290

(22) PCT Filed: Oct. 28, 2002

(86) PCT No.: PCT/FR02/03697

§ 371 (c)(1), (2), (4) Date: Aug. 10, 2005

(87) PCT Pub. No.: WO03/037509

PCT Pub. Date: May 8, 2003

(65) Prior Publication Data

US 2006/0011945 A1 Jan. 19, 2006

(30) Foreign Application Priority Data

Oct. 29, 2001 (FR) .................................. 01 13984

(51) Int. Cl.
*H01B 1/02* (2006.01)
*H01B 1/12* (2006.01)
*H01B 1/06* (2006.01)
*H01J 1/14* (2006.01)
*B01J 27/224* (2006.01)
*B01J 23/00* (2006.01)

(52) U.S. Cl. ........................ 502/178; 502/309; 502/350; 252/516; 252/518.1; 252/520.2; 252/520.5; 252/520.22; 252/521.3

(58) Field of Classification Search ................. 502/178, 502/309, 350; 252/515, 516, 519.12, 520.2, 252/520.21, 520.5, 521.3
See application file for complete search history.

(56) References Cited

U.S. PATENT DOCUMENTS 4,240,087 A * 12/1980 Krause et al. ................. 257/82

(Continued)

FOREIGN PATENT DOCUMENTS

JP 03-151826 * 6/1991

(Continued)

OTHER PUBLICATIONS

"Titania and tungsten doped titania thin films on glass; active photocatalys", by Ashti Rampaul, et al. Polyhedron 22 (2003), pp. 35-44.*

(Continued)

*Primary Examiner*—Jerry Lorengo
*Assistant Examiner*—Patricia L Hailey
(74) *Attorney, Agent, or Firm*—Womble Carlyle Sandridge & Rice, PLLC

(57) ABSTRACT

The photocatalyst based on a composite $WO_3$—$SiC/TiO_2$ semiconductor and subjected to radiation whose wavelength is at least partly less than 400 nm gives1 photocatalytic oxidation of volatile organic compounds and leads to their total mineralisation into $CO_2$ and $H_2O$.

The process for the photocatalytic purification of industrial, agricultural or domestic gaseous effluent may be conducted at room pressure and temperature. Its conversion rate is high and stable.

15 Claims, 4 Drawing Sheets

U.S. PATENT DOCUMENTS

| | | | | |
|---|---|---|---|---|
| 4,427,508 | A | * | 1/1984 | Lichtin .................. 204/157.87 |
| 4,774,026 | A | * | 9/1988 | Kitamori et al. ......... 204/157.4 |
| 4,848,348 | A | * | 7/1989 | Craighead ................... 600/396 |
| 5,130,031 | A | * | 7/1992 | Johnston .................... 210/748 |
| 5,670,247 | A | * | 9/1997 | Takaoka et al. ............. 442/340 |
| 5,961,843 | A | * | 10/1999 | Hayakawa et al. ......... 210/748 |
| 6,074,724 | A | * | 6/2000 | Inaba et al. ................. 428/141 |
| 6,084,109 | A | * | 7/2000 | Chu et al. ................... 549/239 |
| 6,290,180 | B1 | * | 9/2001 | Browall et al. ........... 244/171.7 |
| 6,346,253 | B2 | * | 2/2002 | Takaoka et al. ............. 424/400 |
| 6,585,863 | B2 | * | 7/2003 | Davydov et al. ......... 204/157.3 |
| 7,208,443 | B1 | * | 4/2007 | Kimura et al. .............. 502/232 |

FOREIGN PATENT DOCUMENTS

| | | | |
|---|---|---|---|
| JP | 04-063115 | * | 2/1992 |
| JP | 05-309267 | * | 11/1993 |
| JP | 09-192496 | * | 7/1997 |
| JP | 2000-158455 | * | 6/2000 |
| JP | 2005-271490 | * | 10/2005 |

OTHER PUBLICATIONS

"Photoreduction of Carbon Dioxide and Water into Formaldehyde and Methanol on Semiconductor Materials", by B. Aurian-Blajeni, et al. Solar Energy, vol. 25, pp. 165-170.*

Zorn, M.E. et al 'Photocatalytic oxidation of acetone vapor on TiO2/ZrO2 thin films' Applied Catalysis B: Environmental, vol. 23, p. 1-8 (1999).

Kennedy, J.C. and A.K. Datye, Journal of Catalysis, vol. 179, p. 375-389 (1998).

Serpone, N. et al. "Exploiting the interparticle electron transfer process in the photocatalysed oxidation of phenol, 2-chlorophenol and pentachlorophenol: chemical evidence for electron and hole transfer between coupled semiconductors", Journal of Photochemistry and Photobiology A: Chemistry, vol. 85, p. 247-255 (1995).

Xie, Y.C. et al., Advances in Catalysis, vol. 37 p. 1 (1990).

Database WPI, Section Ch, Week 200220, Derwent Publications Ltd., London, GB, XP-002213957, JP03264317 B, Toto Ltd., Mar. 11, 2002.

Database WPI, Section Ch, Week 199740, Derwent Publications Ltd., London, GB; AN 1997-429732, XP002213958, JP09192496 A, Matsushita Electric Works Ltd., Jul. 29, 1997.

Database WPI, Section Ch, Week 200213, Derwent Publications Ltd. London, GB; AN 1998-280305, XP002213959, JP03255346 B, Toto Ltd., Feb. 12, 2002.

* cited by examiner

US 7,435,702 B2

PHOTOCATALYST AND PROCESS FOR PURIFYING GAS EFFLUENT BY PHOTOCATALYTIC OXIDATION

TECHNICAL FIELD OF THE INVENTION

The present invention concerns the purification of effluent, at room temperature, containing volatile organic compounds (VOCs) by means of a composite $WO_3$—$SiC/TiO_2$ semiconductor that is irradiated. The photocatalyst so formed is illuminated by radiation, whose wavelength is at least partly less than 400 nm. Photocatalytic oxidation of the pollutants leads to total mineralisation into $CO_2$ and $H_2O$.

PRIOR ART

Volatile organic compounds (VOCs) are used or produced in numerous industrial or domestic activities. They are therefore to be found in soils, water and in the air. This raises several environmental and public health problems. Firstly, some VOCs are considered to cause an olfactory nuisance. And a major part of VOCs are considered to be cancerogenic or mutagenic. Finally, the emission of VOCs into the atmosphere is connected with the possible photochemical production of oxidants via the reaction involving VOCs and NOx in the presence of light. Therefore, these reactions lead to an increase in tropospherical ozone which is toxic for man, degrades harvests and is involved in the formation of acid rain. Some VOCs are also involved in the decrease in the stratospherical ozone layer and may contribute towards global warming. Since a high number of VOCs may be oxidized, the heterogeneous catalysis of oxidation could be used for their destruction in effluent. But in general these catalysts operate at high temperatures, which carries disadvantages since provision must be made for heating and temperature regulation devices. It would be simpler if it were possible to conduct reactions at room temperature, that is to say typically between 15 and 30° C.

For the possible destruction of VOCs at room temperature, consideration has been given to the photocatalytic oxidation of gaseous phase organic compounds, using $TiO_2$-based catalysts, whether coupled or not with other semiconductors. By way of example, the photocatalytic oxidation of acetone with a pure $TiO_2$ catalyst or a mixed $TiO_2/ZrO_2$ catalyst at 77° C., prepared in thin layer form using a sol-gel method was described by M. E. Zorn et al in the article "Photocatalytic oxidation of acetone vapor on $TiO_2/ZrO_2$ thin films" published in Applied Catalysis B: Environmental, vol. 23, p. 1-8 (1999). Photocatalysts of $TiO_2$/Pt type have been used to decompose ethanol at a temperature in the region of 200° C. (see J. C. Kennedy and A. K. Datye, Journal of Catalysis, vol. 179, p. 375-389 (1998). A mixed photocatalayst of $TiO_2$/CdS type was tested for the decomposition of phenol, 2-chlorophenol and pentachlorophenol in liquid phase (see N. Serpone et al. "Exploiting the interparticle electron transfer process in the photocatalysed oxidation of phenol, 2-chlorophenol and pentachlorophenol: chemical evidence for electron and hole transfer between coupled semiconductors", Journal of Photochemistry and Photobiology A: Chemistry, vol. 85, p. 247-255 (1995)). German patent application DE 40 23 995 A1 describes semiconductor photocatalysts containing titanium oxide, zinc titanate or oxide, optionally coated with metals such as Pt, Pd, Ir, Rh, Rn, Os, Zn or Ba. This document suggests using these photocatalysts to purify the air inside motor vehicles.

The chief advantage of photocatalysis is that the energy required for oxidation reactions is supplied by direct absorption of light rather than by thermal heating. The photocatalysts used for this purpose are semiconductors having a band gap (optical gap) typically lying between 3 and approximately 4 eV corresponding to light irradiation in the near UV spectral region.

In general, photocatalytic reactions on $TiO_2$ are oxidation-reduction reactions and comprise several main steps:
Adsorption of reagents, of the organic pollutant in particular,
Production of electron-hole pairs through absorption of photons derived from UV radiation,
Spatial separation of electron-hole pairs and migration to the surface of the photocatalyst,
Redox reactions of electrons and holes with the species adsorbed on the surface: reduction of an electron acceptor by the electron, oxidation of an electron donor by the hole;
Desorption of reaction products.

Most often, the electron acceptor which is reduced by the electron is oxygen. The holes may combine directly with the VOCs. But the photocatalytic oxidation of VOCs may also proceed via radicals, such as OH and O.

Heterogeneous photocatalysis using $TiO_2$-based catalysts has several advantages:
i) $TiO_2$ is relatively low cost,
ii) it is not necessary to add other reagents (other than air and the VOC),
iii) the process can be conducted at room temperature and atmospheric pressure,
iv) in general the reaction products are limited to $CO_2$ and $H_2O$.

But $TiO_2$-based photocatalysts also suffer from several disadvantages set forth below.

Problem Raised

Photocatalyst activity in the prior art is limited to the yield of the photocatalytic process itself, and by the too high adsorption of reaction products such as $CO_2$ or possible intermediate oxidation products which may block part of the active sites, leading to degradation of catalyst activity.

Also, the use of a photocatalyst according to the prior art does not always lead to complete VOC mineralisation: with known photocatalysts containing $TiO_2$ it is observed in particular that when the VOC concentration is high, partial oxidation products are formed of which some are toxic.

The problem which this invention attempts to solve is therefore to propose a $TiO_2$-based photocatalyst, with improved and stable yield, for destroying volatile organic compounds in gas effluent by oxidation.

SUBJECTS OF THE INVENTION

The applicant found that the use of a new formulation of photocatalysts containing composite semiconductors of $WO_3$—$SiC/TiO_2$ type bring an improvement in phenomena of reagent adsorption, product desorption and space separation of electron-hole pairs. Therefore, the photocatalytic activity is increased and stabilised compared with known $TiO_2$-based photocatalysts.

One first subject of the present invention is a photocatalyst containing at least two coupled semiconductor compounds, characterized in that one of said semiconductors is titanium dioxide $TiO_2$ and the other is silicon carbide SiC, and in that it also contains tungsten trioxide $WO_3$.

A second subject of the present invention is a preparation method for a $WO_3$—$SiC/TiO_2$ photocatalyst, in two steps, one first step for the simultaneous depositing of $TiO_2$ and SiC on a carrier, and a second step to impregnate said deposit with a solution containing at least one $WO_3$ precursor. Said precursor is then converted into $WO_3$ by calcination.

A third subject of the invention is the use of said photocatalyst in a purification process by photocatalytic oxidation of gas effluent containing volatile organic compounds.

Figure 1:
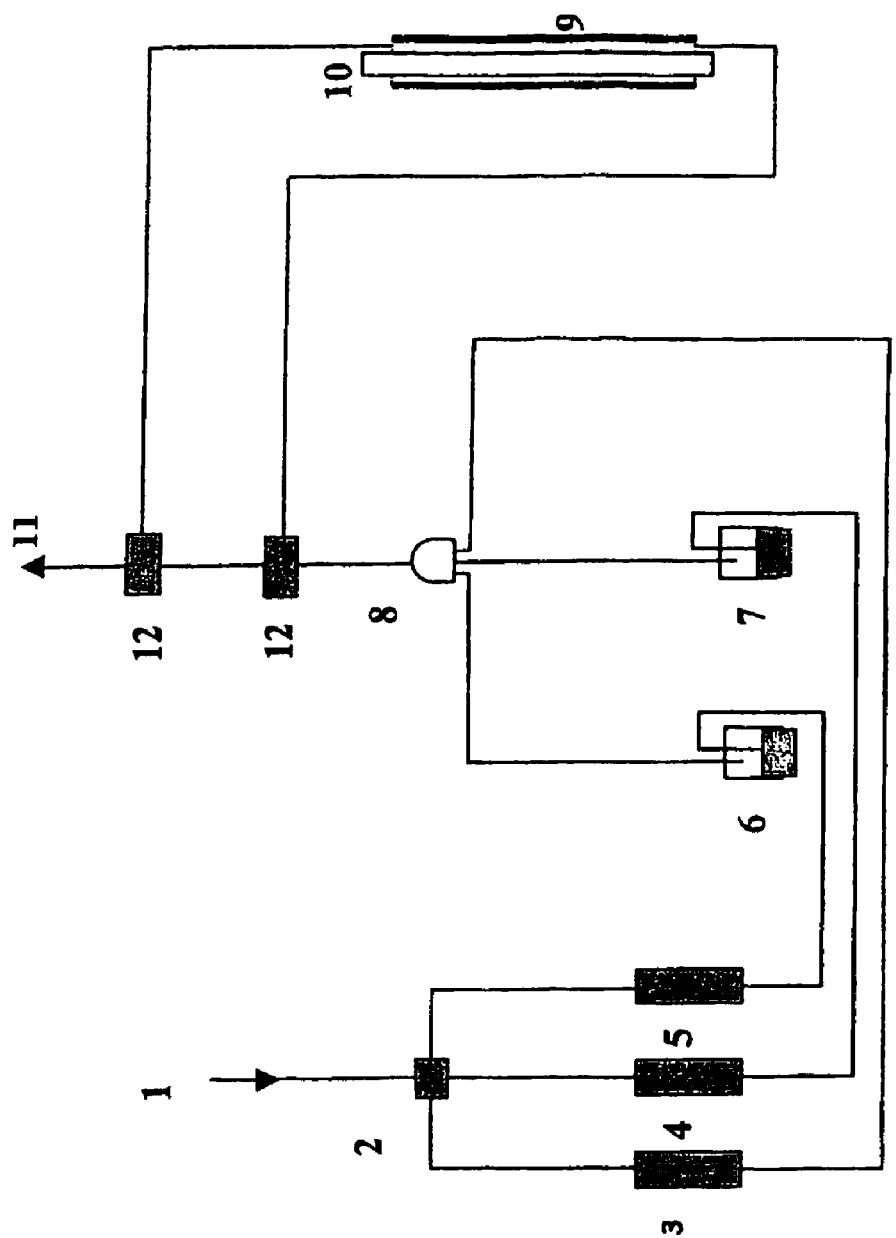
FIG. 1 is a diagram of a reactor used for tests. The following reference numbers are used.

| | |
|---|---|
| Main air inlet | 1 |
| Dispatcher | 2 |
| Dry air duct | 3 |
| Wet air duct | 4 |
| VOC duct | 5 |
| Saturator containing liquid pollutant | 6 |
| Bubble chamber containing liquid water | 7 |
| Mixer | 8 |
| Photocatalytic reactor | 9 |
| Ultraviolet ray lamp | 10 |
| Gaseous phase microchromatograph | 11 |
| Valves | 12 |

FIGS. 2 to 10 relate to tests. Along the Y-axis they show the conversion rate (percent) of the chosen volatile organic compound, and along the X-axis the test time (in seconds for FIGS. 2 to 9, and in hours for FIG. 10), for the different formulations of photocatalysts according to the invention or of the prior art.

DETAILED DESCRIPTION OF THE INVENTION

The photocatalyst of the invention contains at least two coupled, semiconductor compounds. Their band gap (optical gap) preferably lies between 3.0 and 3.2 eV. One of said semiconductors is titanium dioxide, the other SiC. The essential characteristic of the photocatalyst of the invention is that it also contains tungsten trioxide.

In one advantageous embodiment of the invention, the photocatalyst according to the invention contains between 10 and 60% and preferably between 15 and 25% SiC (weight percentages). In another advantageous embodiment, it contains a quantity of $WO_3$ corresponding to 10 to 50% of a theoretical monolayer on $TiO_2$ particles. Said $TiO_2$ advantageously has a BET specific surface area of between 40 and 60 $m^2/g$ and contains between 1 and 5% $WO_3$, preferably between 1.5 and 4% $WO_3$ (weight percentages).

The photocatalyst of the invention may be prepared using a two-step process: a process for preparing a mixed $WO_3$—SiC/$TiO_2$ photocatalyst, comprising at least one first step during which $TiO_2$ and SiC are simultaneously deposited on a carrier, and a second step during which the SiC/$TiO_2$ deposit is impregnated with a solution of a $WO_3$ precursor. This process forms the second subject of the present invention.

The first step of said process consists of simultaneously depositing $TiO_2$ and SiC. During this first step, a first suspension is prepared from $TiO_2$ powder, and a second suspension from SiC powder, the two suspensions are mixed, poured onto a carrier and the solvent is evaporated. As an example of $TiO_2$ powder, a commercially available powder with a BET specific surface area in the order of 50 $m^2/g$ is suitable.

Silicon carbide may be chosen from among different SiC materials, in particular those having a BET measured specific surface area of between 1 and 600 $m^2/g$. The applicant found that a SiC with a specific surface area of between 10 and 100 $m^2/g$, and more particularly between 20 and 50 $m^2/g$, gives good results. Such materials may be prepared for example using the synthesis methods described in the following patents: EP 0 313 480, EP 0 440 569, U.S. Pat. No. 5,217,930, EP 0 511 919, EP 0 543 751 and EP 0 543 752. According to these methods, materials of varied sizes and forms can be synthesized, that is to say in the form of rods, monoliths, extrudates, grains or tubes. These types of SiC give good results, but other forms of SiC may also be used within the scope of this invention.

The desired volumes of each of the two suspensions are sampled and mixed. Advantageously, the quantity of deposited $TiO_2$ is chosen so as to obtain a theoretical coating of 1 $mg/cm^2$ on the carrier. The suspension so prepared is poured onto the carrier and spread homogeneously by heating until complete evaporation of the water. It is preferable to oven dry at 120° C. for 30 minutes. In one preferred embodiment, the carrier is an inner wall of the reactor in which the photocatalyst is used.

During the second step of said process, the $TiO_2$/SiC deposit is impregnated with a solution containing at least one $WO_3$ precursor. This may be made with an aqueous solution of the precursor salt $(NH_4)_{10}W_{12}O_{41}.5H_2O$.

In one advantageous embodiment of the invention, the impregnation protocol and heating of the solution to evaporation is the same as for the first step, including oven drying at 120° C. for 30 minutes. Then calcination is conducted under a flow of air at a temperature of between 300 and 500° C., for example 420° C., for approximately 1 h.

The reactor material under the present invention may be of any type, provided that it is inert. For example tubes in polypropylene, carbon fibre or glass fibre may be used, or even glass or quartz. The use of a material transparent to ultraviolet radiation (quartz for example) is advantageous if the source of UV radiation is located outside the reactor, or if sunlight is used. But it is also possible to consider other radiation passing means, such as a window in material transparent to ultraviolet rays.

The photocatalyst of the invention may be used in a purification process by photocatalytic oxidation for effluent containing volatile organic compounds. This process comprises:
a) adding the gaseous effluent to a reactor containing a photocatalyst of the invention;
b) irradiating said photocatalyst with radiation of which at least part of the light power is emitted along a wavelength of less than 400 nm and preferably less than 360 nm, so that at least part of the volatile organic compounds contained is said effluent is decomposed by oxidation;
c) evacuation of the gaseous reaction mixture from the reactor.

Photocatalytic oxidation of volatile organic compounds (VOCs) is advantageously conducted as a continuous process at room temperature and atmospheric pressure. This makes it possible to use the photocatalyst of the invention directly with the effluent, for example industrial, agricultural or domestic effluent without any particular pre-treatment.

According to one particular embodiment, the process of the invention comprises the addition of oxygen and/or water vapour before they enter the reactor or the simultaneous adding of oxygen and/or water vapour to the reactor.

The effluent entering the reactor may be derived directly from industrial, agricultural or domestic processes, or they may result from a pre-treatment of such effluent. According to one preferred embodiment of the process of the invention, industrial, agricultural or domestic effluent is added which already contains a sufficient quantity of oxygen and water vapour without any addition.

An effluent-purifying device containing volatile organic compounds which may be used within the scope of this invention comprises at least:
- a reactor containing a photocatalyst of the invention;
- a source of ultraviolet radiation;
- means for adding the gaseous effluent to be purified;
- means for evacuating the reaction products.

The UV radiation source is advantageously in the form of one or more tubular UV lamps emitting radiation, characterized in that at least part of its light power is emitted along a wavelength of less than 400 nm and preferably less than 360 nm.

In one preferred embodiment, the photocatalyst is deposited on the light-receiving wall of the photocatalytic reactor, and the UV lamp is arranged inside the photocatalytic reactor. The gaseous effluent circulates in tangential manner between the outer wall of the UV tubes and the inner wall of the reactor. The distance between these two walls is adjusted so as to optimise contact between the gaseous flow and the catalyst surface while minimising load loss.

A ring-type coaxial reactor with the UV lamp arranged inside is suitable for performing the present invention, but this embodiment does not limit the present invention. Different reactor geometries and configurations may be considered. Similarly, the photocatalyst of the invention may be deposited on various carriers.

In another embodiment of the invention, the light power is supplied at least in part by sunlight. In this case, it is possible not to provide the reactor with a technical source of UV radiation, such as an appropriate lamp, the source of UV radiation being the sun. In this case (and in the case in which the technical source of IV radiation is located outside the reactor), the photocatalytic reactor must be provided with means to allow the sun rays to pass; these means may be a window in appropriate transparent material which allows the sunlight to pass, or the reactor may be built using such appropriate transparent material. If sunlight is used, this light may be concentrated and/or focused using optic devices known to persons skilled in the art.

According to the applicant's findings, to ensure optimum decomposition of effluent containing volatile organic compounds, it is advantageous to adjust the chemical composition of the photocatalyst in relation to the nature, and in particular the polarity of the chief organic molecule it is wished to destroy, and in relation to the specific surface area of the $TiO_2$ used. For most VOCs, such as methylethylketone, a $WO_3$ content of between 1.0% and 5.0% (weight percentages) is suitable. This optimum content may be determined by persons skilled in the art by means of a simple routine experiment: a $TiO_2$ with a large specific surface area will require a higher $WO_3$ content than a $TiO_2$ with a low specific surface area. A $WO_3$ content that is too high risks masking the $TiO_2$ which will reduce the efficacy of the catalyst, since part of the light is absorbed by the $WO_3$.

By way of example, for a $TiO_2$ with a BET specific surface area of 50 $m^2/g$, since for $WO_3$ the theoretical monolayer corresponds on average to 0.21 $g/100\ m^2$ of carrier [see Y. C. Xie, Y. Q. Tang in Advances in Catalysis, vol. 37 page 1 (1990)], the optimum $WO_3$ content lying between 0.1% and 5.0% therefore corresponds to approximately 10 to 50% of the theoretical monolayer.

The optimum SiC content, which is less critical however, and the type of SiC initially used may also be determined by means of a simple routine experiment.

The process may be used for the purification of industrial, agricultural or domestic effluent. By way of example gaseous effluent derived from a tannery, which causes a definite olfactory nuisance, was successfully treated using the process of the invention. In this effluent, the chief VOCs were methylethylketone and butyl acetate. Treatment was conducted at room temperature (i.e. at a temperature typically lying between 15 and 30° C.) and at room pressure (i.e. atmospheric pressure) which is advantageous since the reactor can then be of very simple, sturdy design. A flow of industrial gas waste of up to 10 000 $m^3/h$ was successfully treated in this manner in a prototype reactor. The applicant also found that with the photocatalyst of the invention it is possible to disinfect the gaseous flow passing through it; therefore it can be used to inactivate microorganisms such as bacteria or viruses contained in the air.

The invention will be better understood with the help of the examples which are not, however, of a limitative nature.

EXAMPLES

In these examples, all percentages concerning the chemical composition of the photocatalyst are weight percentages.

A diagram of the reactor used for tests is shown in FIG. 1. The photocatalytic reactor 9 was of ring type. The source of ultraviolet radiation 10 was a tubular lamp mounted coaxially inside the reactor; the radiation wavelength was centred on 350 to 360 nm.

The main air inlet 1 is divided into three ducts by means of a dispatcher 2. The flow rate in each of the three ducts, dry air 3, wet air 4 and VOC 5 is fixed by means of a mass flowmeter. The air is saturated with water vapour when passing through a bubble chamber containing liquid water 7 and with VOCs by means of a saturator containing liquid pollutant 6. After fixing the flow rates in each duct and therefore the VOC concentrations and relative humidity, the entire flow passes through a mixer 8. By means of valves 12 the reaction mixture can then be directed either to the catalyst 9 irradiated by UV radiation 10, followed by gaseous phase microchromatography for analysis of the reaction products, or directly onto the microchromatograph for analysis of the initial gaseous composition.

Different formulations of the $WO_3$—SiC/$TiO_2$ catalysts were tested, by varying their relative $WO_3$ and SiC concentrations. The SiC was extruded, washed, oven dried, calcined at 700° C. and then crushed. The $TiO_2$ used was a commercially available powder (supplier: Prolabo) and the SiC was obtained according to the method described in patent EP 0 543 751 A1, whose invention permits the synthesis of metal carbides and silicon having a high specific surface area by causing a volatile oxide of silicon, SiO, to react with carbon of high specific surface area at a temperature of between 900 and 1400° C. in a stream of inert gas.

Different experiments, denoted 1, 2, 3, 4, 5, 6, 7 8 and 9 were performed, all with humidity contents of 50%. The control volatile organic compound was methylethylketone (MEK) to the proportion of 1500 ppm (weight ppm). The tests were conducted in a continuous reaction mixture for times ranging from 40 min to 18 hours.

Experiments 1, 2, 3 and 4 concern the influence of the nature of the different $TiO_2$, $WO_3$ and SiC materials.

Figure 2:
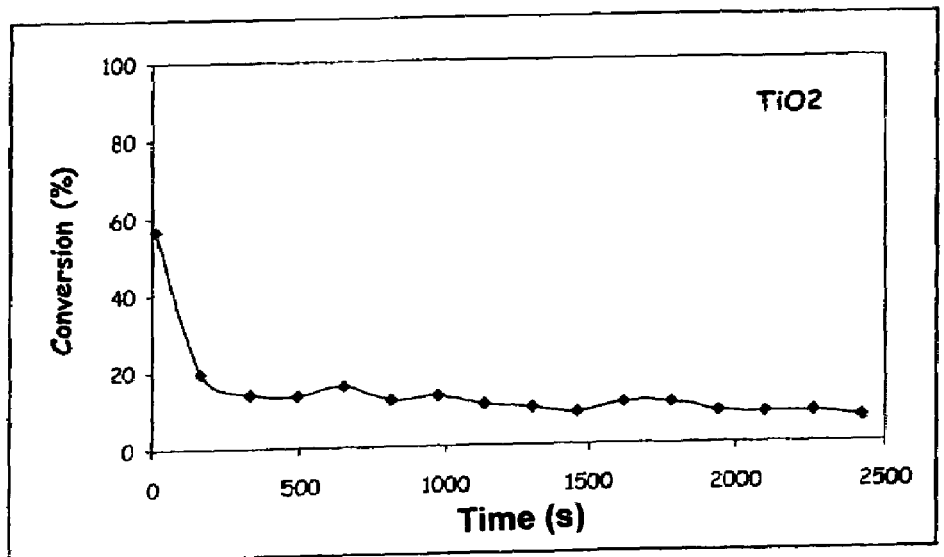

Experiment 1 was conducted on a $TiO_2$ catalyst alone (FIG. 2).

Figure 3:
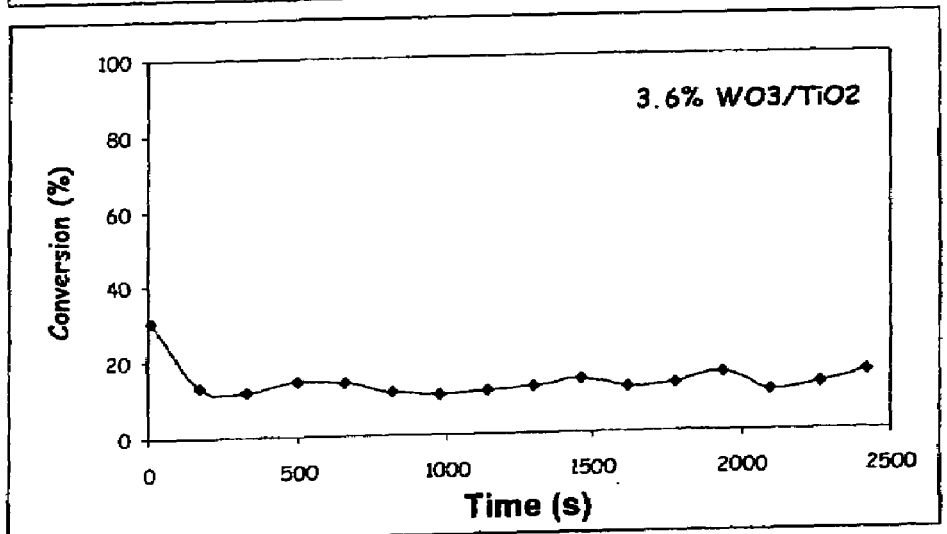

Experiment 2 was conducted on a 3.6% $WO_3$/$TiO_2$ catalyst (FIG. 3).

Figure 4:
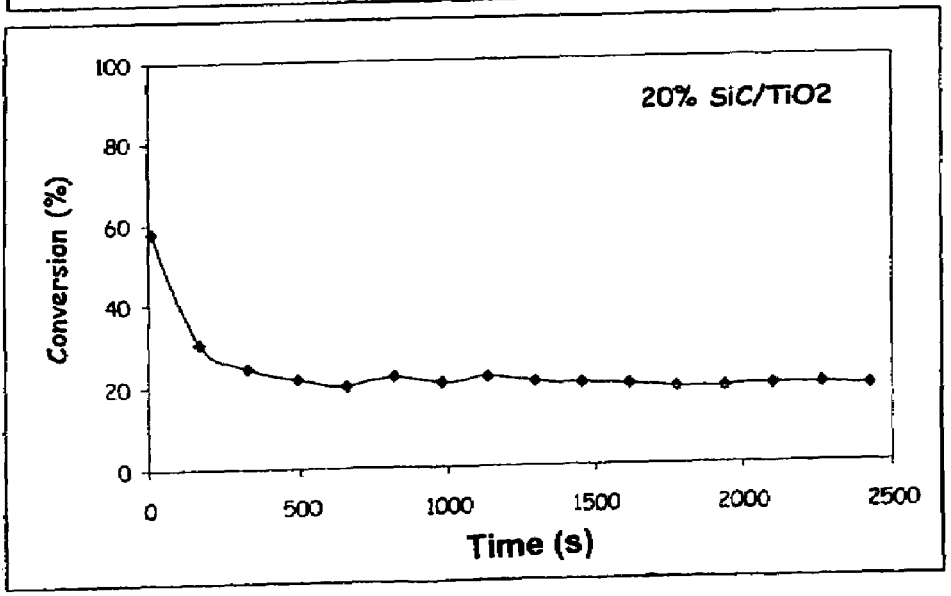

Experiment 3 was conducted on a 20% SiC/$TiO_2$ catalyst (FIG. 4).

Figure 5:
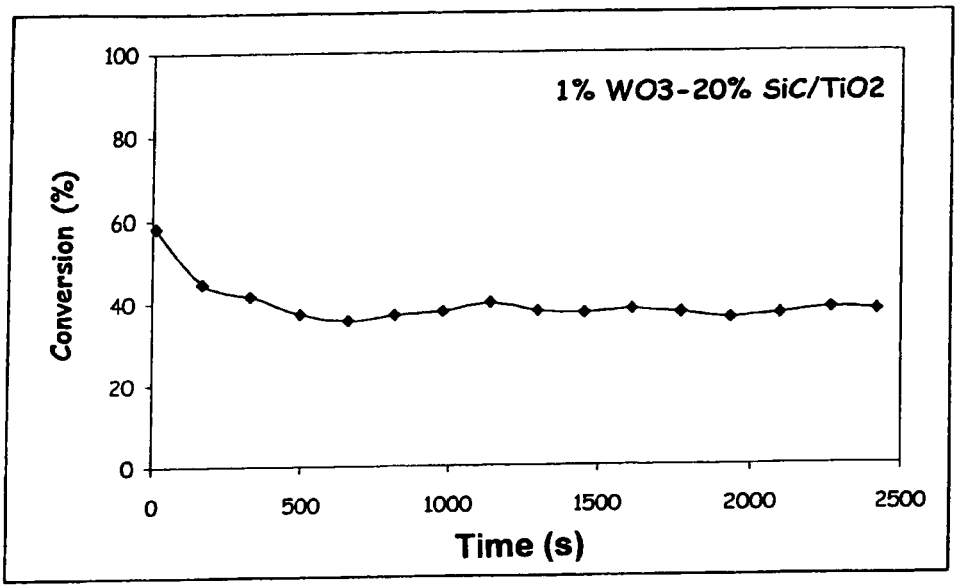

Experiment 4 was conducted on a 1% $WO_3$-20% SiC/$TiO_2$ catalyst (FIG. 5).

Experiments 5, 6 and 7 examine the influence of the tungsten oxide content.

Figure 6:
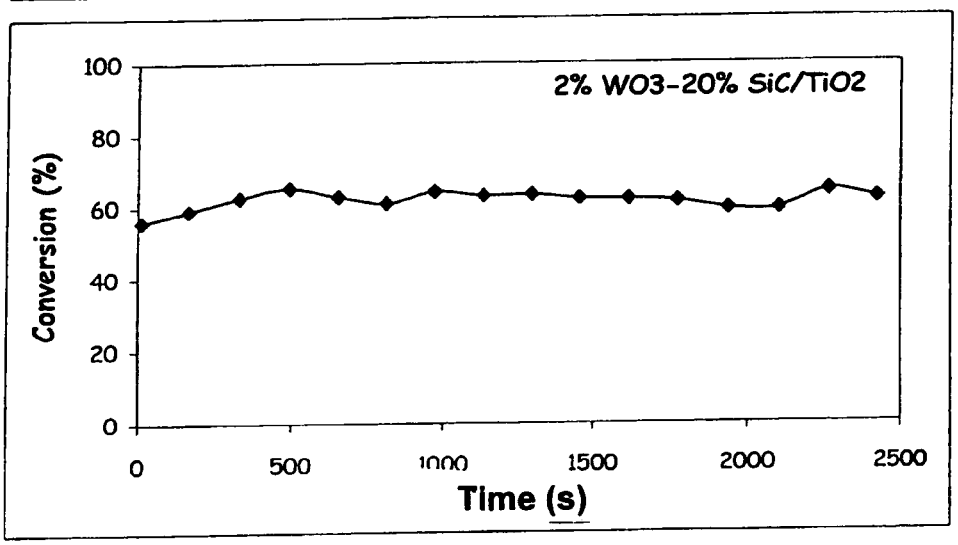

Experiment 5 was conducted on a 2% $WO_3$-20% $SiC/TiO_2$ catalyst (FIG. 6).

Figure 7:
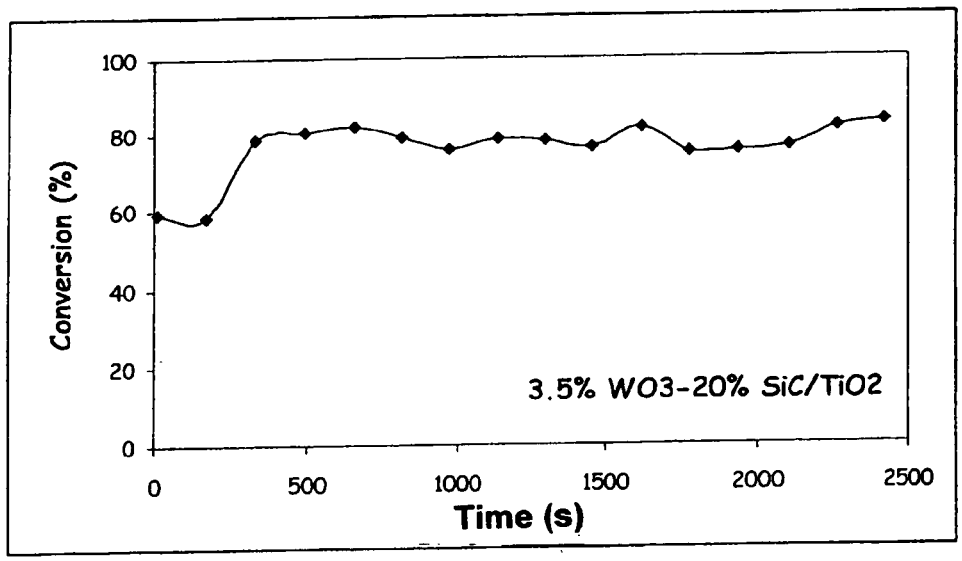

Experiment 6 was conducted on a 3.5% $WO_3$-20% $SiC/TiO_2$ catalyst (FIG. 7).

Figure 8:
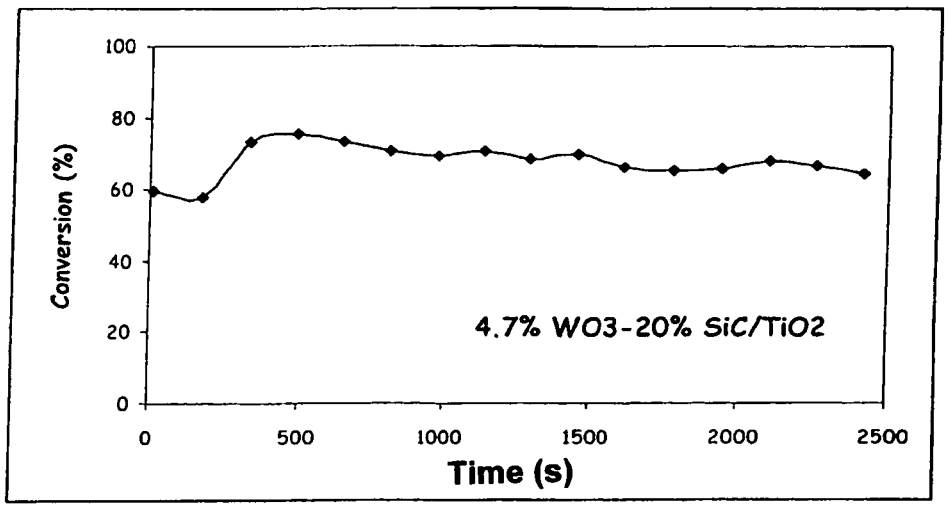

Experiment 7 was conducted on a 4.7% $WO_3$-20% $SiC/TiO_2$ catalyst (FIG. 8).

Figure 9:
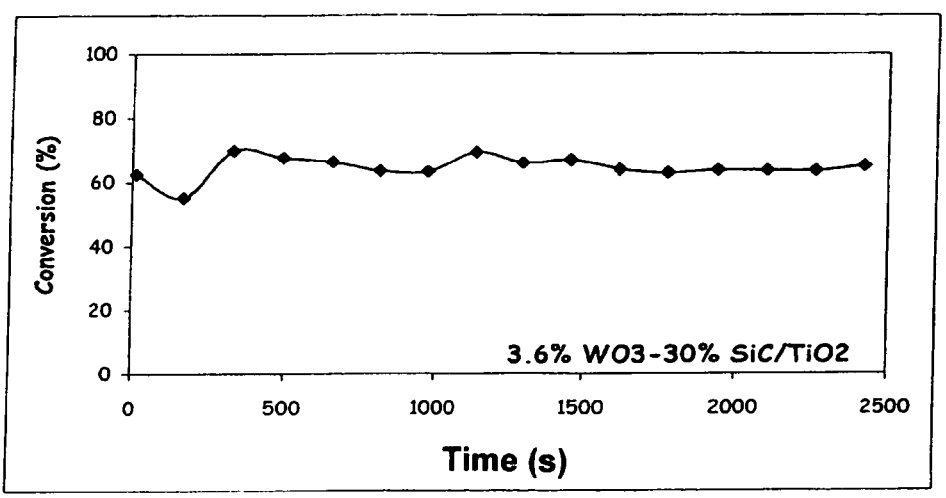
Figure 10:
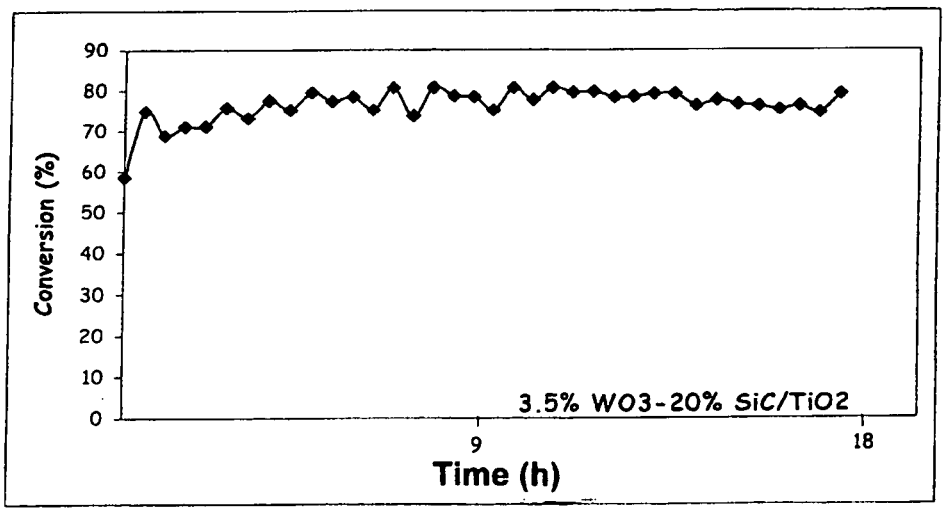

Experiment 8 concerned the influence of SiC content. It was conducted using the 3.6% $WO_3$-30% $SiC/TiO_2$ catalyst (FIG. 9).

Experiment 9 is a study of the stability of the composite catalyst in a reaction mixture. It was conducted using a 3.5% $WO_3$-20% $SiC/TiO_2$ catalyst (FIG. 10) after more than 18 hours in a reaction mixture.

Even though the initial conversion was approximately 60% on $TiO_2$ alone (FIG. 2), this catalyst is not very efficient in destroying the pollutant, since it rapidly deactivates in time in a reaction mixture, to arrive at conversion rates in the region of 10%. The addition of 3.6% $WO_3$ to $TiO_2$ does not improve the photocatalytic performance of the system (FIG. 3). The use of the composite semiconductor catalyst, 20% $SiC/TiO_2$ leads to a slight improvement compared with $TiO_2$ alone (experiment 3, FIG. 4) since conversion rates of approximately 20% are achieved after approximately 1000 to 2000 seconds. On the other hand, the addition of $WO_3$ and SiC to $TiO_2$ (FIGS. 5, 6, 7, 8 and 9) results in a considerable increase in VOC photooxidation, depending upon $WO_3$ and SiC content. It was found that the optimum weight percentage of SiC is 20% and that of $WO_3$ is 3.5%. Therefore the optimum formulation of the photocatalyst to decompose methylethylketone is 3.5% $WO_3$-20% $SiC/TiO_2$. Under these conditions, after three minutes start-up, 80% of the pollutant is converted to $CO_2$ and $H_2O$. By increasing the relative proportions of SiC and $WO_3$, this activity is reduced.

Experiment 9 (FIG. 10) shows the performance of the 3.5% $WO_3$-20% $SiC/TiO_2$ catalyst in a continuous flow of methylethylketone for more than 18 hours. It is observed that there is no deactivation of the catalyst, which corresponds to a substantial improvement compared with the prior art.

Additional tests, conducted under the same conditions as above, were able to show that a photocatalyst with 50% SiC and 3.4% $WO_3$ gives a conversion rate over approximately 2 000 seconds in the order of 40%, and a photocatalyst with 8% SiC and 3.5% $WO_3$ gives a result that is substantially equivalent to the result observed in experiment 3.

The invention claimed is:

1. A photocatalyst containing:
   at least two coupled semiconductor compounds, wherein the at least two coupled semiconductor compounds comprise titanium dioxide, $TiO_2$, and silicon carbide, SiC, and wherein the SiC constitutes between 10 and 60 weight % of the photocatalyst; and
   tungsten trioxide, $WO_3$.

2. A photocatalyst according to claim 1, wherein the photocatalyst contains a quantity of $WO_3$ corresponding to 10 to 50% of a theoretical monolayer relative to the BET specific surface area of $TiO_2$ particles.

3. A photocatalyst according to claim 2, wherein the photocatalyst contains $TiO_2$ having a BET specific surface area of between 40 and 60 $m^2/g$, and wherein the photocatalyst contains between 1 and 5 weight %.

4. A photocatalyst according to claim 2, wherein the photocatalyst contains SiC having a BET specific area between 1 and 600 $m^2/g$.

5. A photocatalyst according to claim 2, wherein the photocatalyst contains $TiO_2$ having a BET specific surface area of between 40 and 60 $m^2/g$, and wherein the photocatalyst contains between 1.5 and 4 weight % $WO_3$.

6. A photocatalyst according to claim 2, wherein the photocatalyst contains SiC having a BET specific surface area between 10 and 100 $m^2/g$.

7. A photocatalyst according to claim 1, wherein the photocatalyst contains $TiO_2$ having a BET specific surface area of between 40 and 60 $m^2/g$, and wherein the photocatalyst contains between 1 and 5weight % $WO_3$.

8. A photocatalyst according to claim 7, wherein the photocatalyst contains SiC having a BET specific area between 1 and 600 $m^2/g$.

9. A photocatalyst according to claim 1, wherein the photocatalyst contains SiC having a BET specific area between 1 and 600 $m^2/g$.

10. A photocatalyst according to claim 1, wherein the photocatalyst contains $TiO_2$ having a BET specific surface area of between 40 and 60 $m^2/g$, and wherein the photocatalyst contains between 1.5 and 4 weight % $WO_3$.

11. A photocatalyst according to claim 1, wherein the photocatalyst contains SiC having a BET specific area between 10 and 100 $m^2/g$.

12. A process for preparing a mixed $WO_3$—$SiC/TiO_2$ photocatalyst, comprising:
    in at least a first step, simultaneously depositing $TiO_2$ and SiC on a carrier; and
    in a second step, impregnating the $SiC/TiO_2$ deposit with a solution containing at least one $WO_3$ precursor.

13. A process according to claim 12, wherein, during the first step:
    a first suspension is prepared from $TiO_2$ powder;
    a second suspension is prepared from SiC powder;
    the first and second suspensions are mixed to form a mixture including a solvent and are thereafter poured onto the carrier; and
    the solvent is evaporated.

14. A process according to claim 12, wherein the $WO_3$ precursor solution is an aqueous solution of $(NH_4)_{10}W_{12}O_{41}5H_2O$.

15. A process according to claim 12, comprising:
    in a third step, conducting calcination at a temperature between 300 and 500° C.

* * * * *